(12) United States Patent
Moyes

(10) Patent No.: US 6,459,279 B2
(45) Date of Patent: Oct. 1, 2002

(54) DIAGNOSTIC TESTING EQUIPMENT FOR DETERMINING PROPERTIES OF MATERIALS AND STRUCTURES OF LOW OBSERVABLE VEHICLES

(75) Inventor: Tom Moyes, Valencia, CA (US)

(73) Assignee: Lockheed Martin Corporation, Palmdale, CA (US)

( * ) Notice: Subject to any disclaimer, the term of this patent is extended or adjusted under 35 U.S.C. 154(b) by 0 days.

(21) Appl. No.: 09/879,464

(22) Filed: Jun. 13, 2001

Related U.S. Application Data

(63) Continuation-in-part of application No. 09/261,756, filed on Mar. 2, 1999, now abandoned.

(51) Int. Cl.$^7$ .......................... G01R 27/32; G01R 27/04
(52) U.S. Cl. ..................... 324/644; 324/632; 324/637; 324/642
(58) Field of Search .................. 324/644, 637, 324/642, 654, 649, 658, 718, 716, 632; 330/149, 110

(56) References Cited

U.S. PATENT DOCUMENTS

| | | | | |
|---|---|---|---|---|
| 3,102,232 A | * | 8/1963 | Leonard et al. | 324/644 |
| 3,867,697 A | * | 2/1975 | Vanzetti et al. | 324/752 |
| 4,691,198 A | * | 9/1987 | Mortensen | 340/649 |
| 5,497,098 A | * | 3/1996 | Heil et al. | 324/637 |
| 5,652,522 A | * | 7/1997 | Kates et al. | 324/642 |
| 5,847,567 A | * | 12/1998 | Kielb et al. | 324/642 |
| 5,851,083 A | * | 12/1998 | Palan | 333/254 |

* cited by examiner

Primary Examiner—N. Le
Assistant Examiner—Anjan K. Deb
(74) Attorney, Agent, or Firm—Lockheed Martin Corporation

(57) ABSTRACT

A hand held diagnostic test device enables determination of the integrity of low observable (L.O.) properties in structures or surfaces of a structure, and includes a housing containing a first component for coupling energy signals into the structure or a surface of the structure, a second component for detecting the response energy signals, a third component for determining whether the response energy signals indicate flaws in the surface of the structure, and a fourth component for signaling an operator of the diagnostic test device of the results. The energy signal is an RF signal, and a microprocessor in the test device enables determination of the integrity of the structure of surface by comparing the returned signals against a stored acceptable signal. Acceptability or non-acceptability is signaled to the operator of the diagnostic test device by indicator lamps located on the sensor housing and/or a digital display.

20 Claims, 2 Drawing Sheets

DIAGNOSTIC TESTING EQUIPMENT FOR DETERMINING PROPERTIES OF MATERIALS AND STRUCTURES OF LOW OBSERVABLE VEHICLES

CROSS REFERENCE TO RELATED APPLICATIONS

This application is a continuation-in-part of U.S. patent application Ser. No. 09/261,756, filed on Mar. 2, 1999 to T. Moyes now abandoned.

BACKGROUND OF THE INVENTION

1. Field of the Invention

The present invention relates generally to diagnostic equipment, and more particularly to apparatus for performing diagnostic tests on materials and/or structures to determine integrity of properties in low observable vehicles.

2. Description of Related Art

Typically, stealthy or "low observable" (L.O.) vehicles, and in particular, aerostructures, are provided with radar absorbing materials (RAM) in the form of structures or coatings having low radar visibility properties. They are also provided with radar reflective materials for controlling radar visibility properties, such as coatings on transparences, canopies, light lenses, optical sensor apertures, IR sensor apertures, conductive fillers, and conductive tapes. These L.O. materials historically experience failure, e.g. in the form of cracks, or damage, e.g. environmental effects such as wind, rain, hail, sun or thermal stresses. Additionally, such materials are known to be damaged through improper repair techniques.

In the use of such materials, it is desirable to be able to identify the location of such failures or damage so that repairs, replacement or covering of the failed or damaged locations can be effected with new materials or coatings. The identification and location of such failures has traditionally been achieved by specially trained engineers who use diagnostic equipment that require expert interpretation of the output. Against this background, the inventors have developed a diagnostic tool that will indicate with substantial precision the presence of failures in low observable (LO) structures and materials using a hand-held detection apparatus that quickly and easily indicates the status of LO integrity.

Existing art devices are limited in the scope of functions that they can perform and by environmental and ergonomic operational considerations. The present invention avoids these limitations by being multifunctional and applicable to environmental and ergonomic conditions that are beyond the capabilities of existing art devices.

Existing art devices traditionally are limited to use in a laboratory or manufacturing environment due to the safety issue of the explosive fuel environment that is found around operational aircraft. These devices use off the shelf equipment that contains high voltages and switches that are ignition sources. The present invention avoids this serious operational limitation by using sealed switches (power and function), sealed battery compartments and low voltages designed to allow the present invention to be operationally safe and efficient when used within explosive environments (fuel vapor) found around operational aircraft.

Additionally, such devices function is limited to identifying if the work piece is conductive, insulative or coated with radar absorbing material. The present invention avoids these limitations by additionally displaying the surface conductivity of the work piece and also by indicating whether the work piece is within specification, that is, whether the work piece is coated with radar absorbing material or not.

Existing devices use transmission line technology (waveguide, parallel plate, coaxial, or strip-line) or antenna technology to launch and receive RF or microwave energy to/from the item under test. The present invention avoids the limitations associated with such transmission technologies by using a two port RF or microwave structure that is made up of lumped and/or distributed inductance and capacitance (an RF or microwave circuit) as a sensor. This structure produces localized electric and magnetic fields that induce voltages and currents within the material under test. These voltages and currents within the material under test create electric and magnetic fields that are dependent on the electrical properties of the material under test. The fields thus produced by the material under test and sensor interact constructively and/or destructively thus altering the frequency, amplitude, and phase response of the sensor. Thus the properties of the material under test can be determined from the response of the sensor to the material under test. The configuration of the RF or microwave circuit is selected and optimized for the types of materials that are being tested.

Existing art devices are single function devices, whereas the present invention is multifunction. The maintainers of Low Observable (LO) vehicles require multifunctional tools to reduce operator training and simplify maintenance inspections. The desired functions are all performed by the present invention:

a) Conductive Materials
   Surface resistance readout
   Pass/Fail indicator
b) Absorptive Materials
   Type of absorptive material
   Material electrical properties
   Backing type-conductive/nonconductive
   Conductive Backing Quality (resistance readout)
   Material thickness Finally existing art devices can and often do produce repetitive motion injuries due to their weight and awkward hand positioning that is sometimes required during their normal use. Such motion injuries are caused by repetition, force and awkward reach (position). The present invention reduces force by reducing the weight of the portion of the device that is hand held. This is accomplished by separating the device into two portions. A lightweight sensor head that is connected to a belt pack unit with a lightweight cable. Awkward reach (position) is reduced through the use of bellows to self align the sensor with the surface under test and the ability to mount the sensor head on an extension pole reduces awkward position and reach.

OBJECTS AND SUMMARY OF THE INVENTION

It is therefore an object of the present invention to provide a novel intelligent, hand-held, diagnostic tool that will quickly and readily enable an inexperienced user to determine whether low observable properties in vehicle structures are present, absent, or substantially flawed, while overcoming many of the disadvantages and drawbacks of similar previously known diagnostic tools. Thus the present invention is capable of safe and efficient operation in potentially difficult/hazardous environments (explosive and/or toxic), such as fuel vapor areas, flight lines etc., found around operational aircraft.

Yet another object of the present invention is to provide a novel hand held, v diagnostic test device having a sensor unit with "Pass"/"Fail" indicator lights and a digital display located on the sensor head for indicating whether Radar Cross Section (RCS) performance has been degraded by damage, repairs or normal wear and tear, and a bellows on the sensor for insuring positioning of the sensor flush against the surface or structure of which the RCS properties are to be measured.

Still another object of the invention is to provide a novel diagnostic tool, which includes a sensor an/or sensors, "intelligence" electronics and software for determining the integrity of low observable properties in materials and structures of various vehicles, particularly aerostructures.

DETAILED DESCRIPTION OF THE INVENTION

The following description is provided to enable any person skilled in the art to make and use the invention, and sets forth the best modes contemplated by the inventor of carrying out his invention. Variations, however, may be readily apparent to those skilled in the art, since only the generic principles of the present invention have been defined herein specifically to provide teachings for a diagnostic tool that encompasses many long sought after features.

Figure 1:
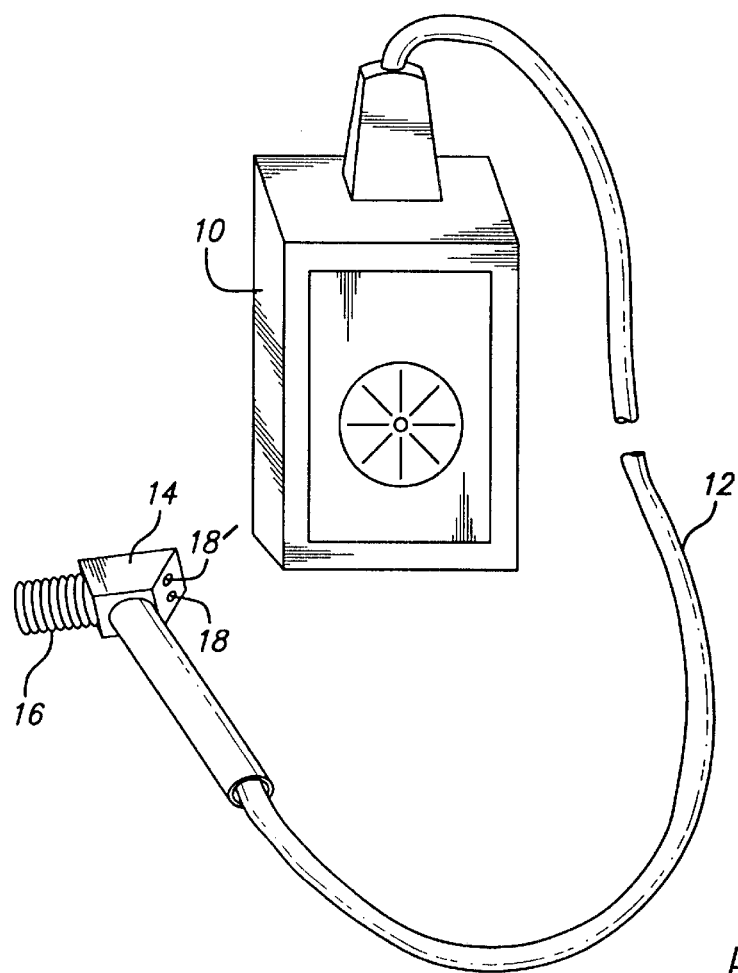
FIG. 1 depicts the hand-held diagnostic tool according to the present invention.

Referring now to FIG. 1, the diagnostic tool of the present invention is seen to include a housing 10 for containing electronic components (not shown here but schematically seen in FIG. 2) and firmware for controlling operation of the components, wiring 12 connected at one end to the meter housing, and a sensor head assembly 14 connected at the opposite end of the wiring. The sensor head assembly includes a sensor 16, a bellows shroud for containing the sensor, and indicator lights 18,18'. Preferably, the indicator lights will be a "Pass" green diode and a red "Fail" diode.

Figure 2:
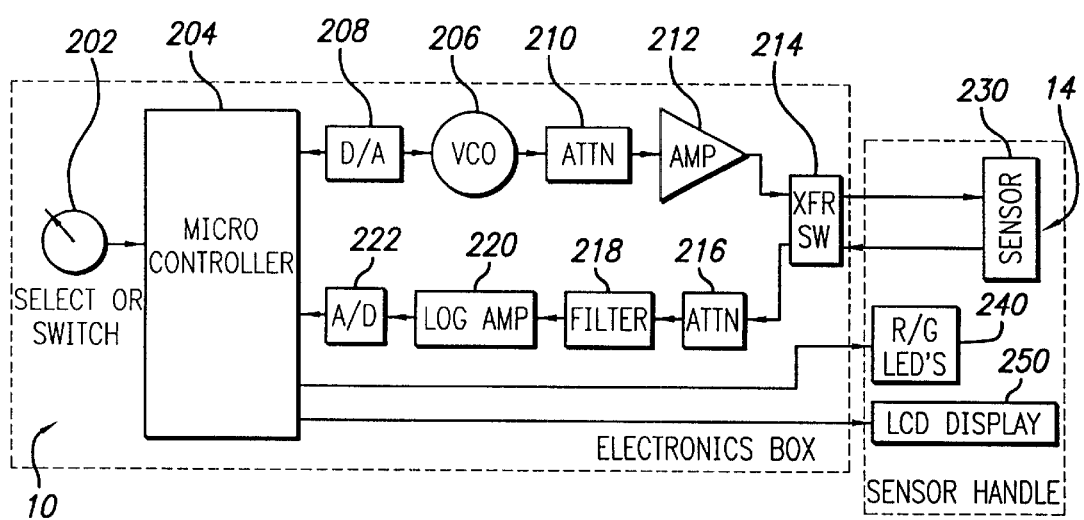
FIG. 2 is a block diagram showing the principle electronic components of which the diagnostic tool of the present invention is comprised.

FIG. 2 shows a block schematic diagram of the electronic components of which the diagnostic tool of the present invention is comprised. The diagnostic tool includes an electronics box 10 and a sensor head 14. A selector switch 202 can be set in one of a plurality of positions, each of which provides a signal to a microcontroller 204 thereby directing the microcontroller to perform a specific function. The microcontroller commands a voltage controlled oscillator (VCO) 206 to issue the requisite stimulus frequency for the sensor 230 by way of the digital-to-analog converter 208. An attenuator 210 and an amplifier 212 isolate the sensor from the VCO 206, in order to prevent the VCO from providing changes in sensor loading that could cause a frequency pulling of the VCO. The attenuator 210 is set such that the amplifier is operated slightly beyond its 1 dB compression region so that it acts as a soft limiter. This amplifier mode produces extremely flat output power as a function of frequency for the type of amplifier Preferably, the VCO and amplifier are selected for their temperature stability. The transfer switch 214 allows the stimulus signal to be sent either to the sensor or back (loop back mode) into the detector circuit to facilitate a "built in" test capability of the RF electronics and a compensation capability for slight drifts that occur during normal operation. The stimulus signal that passes through the sensor 230 is returned and passes through a second attenuator 216 that acts as a passive isolator to protect the detector log video amplifier circuitry 220 from changes in sensor load. The filter 218 removes any second harmonic of the VCO, and serves to remove "out of band" EMI from the signal sent to the sensor that might contaminate the measurement. It is noted that the demodulation log amp is very broadband, and would process these signals if the filter were not there. The demodulating log amp converts the RF signal into a DC signal having amplitude proportional to the log of the input RF signal. Typically passive diode detectors are used in hand held devices as part of the receiver circuit. However, insofar as they are not temperature stable, they can be subjected to a heater to warm them up (but this requires lots of power). The signal from the log amp is converted into a digital signal for the microcontroller by the A/D converter 222. The data is analyzed by the microcontroller and the results of the analysis are indicated to the operator on the LED's 240 and or numeric display 250.

The invention contemplates a sensor assembly which has small lightweight sensors on one end, said assembly having the capability of being attached to a telescoping rod or shaft, and a small box containing the RF electronics and a removable battery pack (commercial "D" sized batteries have been used in the apparatus of the invention) on the operator's end. This multiple portion or component design for the device or tool of the present invention greatly reduces the occurrence of repetitive motion injuries. With this design force is reduced by reducing the weight on the portion of the tool or device that is hand held.

Additionally, it is contemplated that multiple sensor assemblies may be utilized as well as sensor assemblies with multiple plug in sensor elements. Additionally, such sensor assemblies can be attached to a telescoping rod or shaft for the convenience of application use. "Pass" and "Fail" indicator diode lights and/or a digital display are located on the sensor head to allow the operator to immediately determine test results without having to divert his or her attention from the test object. Since the sensor must be flush against the surface of the object being tested, a bellows is placed about the sensor head.

The sensors are used to launch RF energy into or across the material or assembly under test, and detect its response to the energy. The sensing devices are optimized for particular material or assembly to be tested or inspected. Sensor size, configuration, frequency response, etc., is determined by both the characteristics of the failure response and the physical configuration of the component being tested or inspected. Typically, sensors are sized to locate small anomalies, and are ergonomically designed for ease of use in the field.

The firmware for the microcontroller ties the whole system together into a practical tool for field use and performs several functions.

One is a "Power On" self test to verify proper operation of the RF electronics and sensor assembly. This involves setting the transfer switch to the "loop back" position and directing a sample of the stimulus signal to the detector circuit, where it is compared to a stored trace signal set at the factory. The transfer switch is then set to send the stimulus signal to the sensor and the RF response of the sensor is verified. A free space calibration of the sensor is then performed. The selector switch has a calibration setting that allows the operator to redo the free space calibration during normal operation to compensate for any slight drifts that may occur. Another function of the firmware is the generation of the stimulus signals for the type of test that is being performed. Yet another function is the analysis of the data to produce a pass/fail indication on the sensor LEDs or a digital readout on the LCD panel. The stimulus signal is a step frequency signal generated by the microcontroller according to an algorithm. Each step of the detected waveform is processed by another algorithm that has the pass/fail criteria for the type of test that has been selected.

The firmware allows the operator to select a specific test, and then with no additional operator input configures the equipment for that test, calibrates the system, and sets pass/fail criteria. In addition, the firmware performs health checks and data analysis, all transparent to the operator. The operator turns the equipment on, selects the test, and is given a "Pass" or "Fail" test result, or a numerical readout, corresponding to the type of test being performed.

Figure 3:
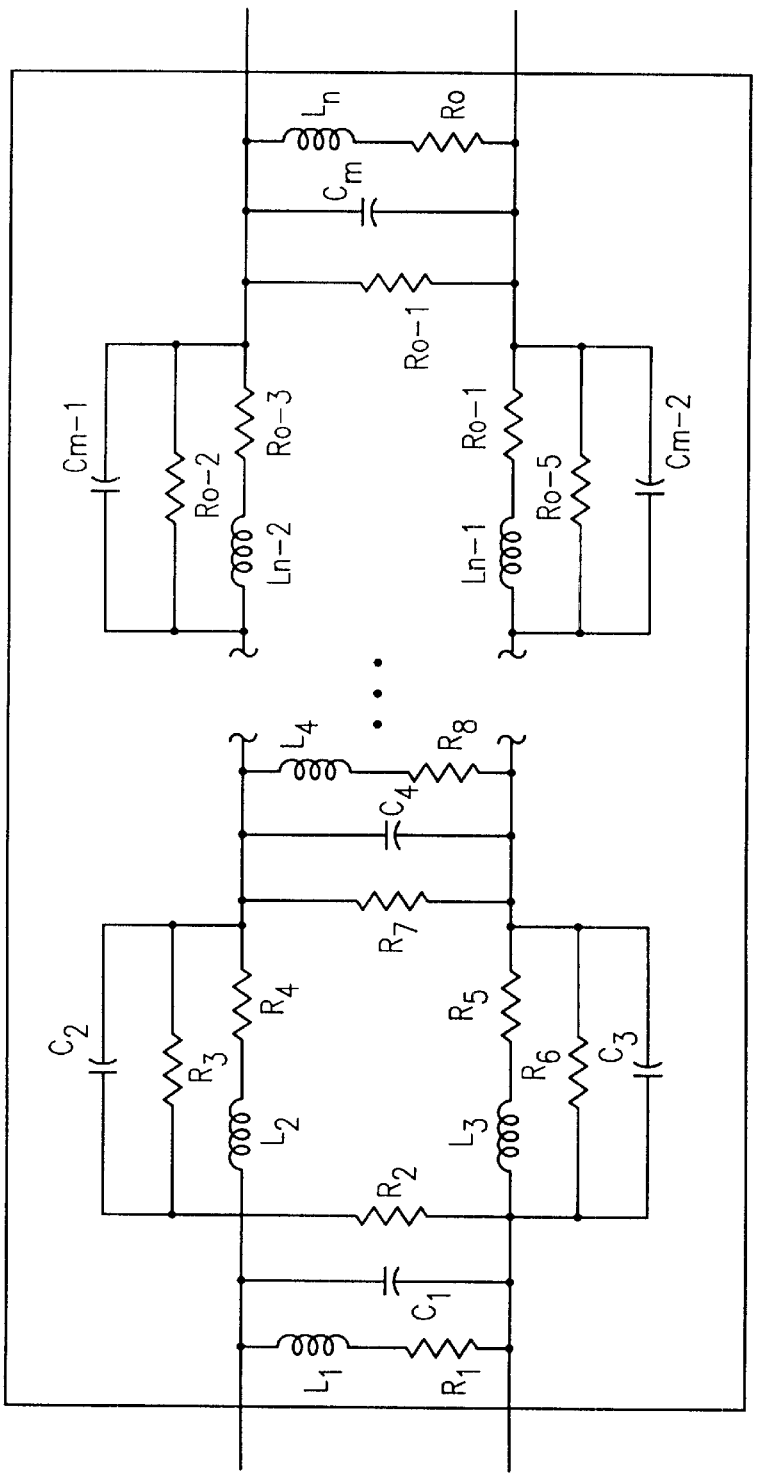
FIG. 3 is a general schematic circuit diagram of the Two Port RF Network of the present invention.

Preferably, all of the major electronic components are operable in an extended temperature range of −40 to +85 degrees C., a range currently identified as the desired temperature range for ground support equipment. Preferably, the configuration of the sensor is a two-port RF or microwave structure, as shown in a generalized circuit diagram in FIG. 3. This RF structure is made up of lumped and/or distributed inductance and capacitance (an RF or microwave circuit) as a sensor. This structure produces localized electric and magnetic fields that induce voltages and currents within the material under test. These voltages and currents within the material under test create electric and magnetic fields that are dependent on the electrical properties of the material under test. The fields thus produced by the material under test and sensor interacts constructively and/or destructively thus altering the frequency, amplitude, and the phase response of the sensor. The properties of the material under test can be determined from the response of the sensor to the material under test. The configuration of the RF or microwave circuit is selected and optimized for the types of materials that are being tested.

A stimulus signal, generated by the electronics drives one port. The electrical response to the stimulus signal is obtained from the other port. The response is determined by the electromagnetic interaction with the sensor and the material under test. The response obtained is dependent on the electromagnetic properties of the material under test and therefore provides an indicator of material performance.

Those skilled in the art will appreciate that various adoptions and modifications of the invention as described above can be configured without departing from the scope and spirit of the invention. Therefore, it is to be understood that, within the scope of the appended claims, the invention may be practiced other than as specifically described herein.

What I claim is:

1. A hand-held diagnostic test device for determining integrity of low observable properties in a structure, comprising:
    means for generating radio frequency energy signals;
    means for coupling the radio frequency energy signals into a surface of said structure to elicit a response to said radio frequency energy signals,
    a detector log amplifier for detecting the response to said radio frequency energy signals,
    means for determining whether the response to said radio frequency energy signals indicates flaws in the surface of said structure, and
    means for indicating the presence of flaws in the surface of said structure.

2. The diagnostic test device of claim 1, further comprising means for allowing said device to be used in an explosive environment including sealed switches, a sealed battery compartment and low voltages.

3. The diagnostic test device of claim 1, wherein:
    the device comprises multiple lightweight portions, including a lightweight sensor head that is connected to a belt pack unit with a lightweight cable.

4. The diagnostic test device of claim 1, wherein said means for coupling radio frequency energy signals into the surface of said structure comprises a two port network that further comprises lumped and/or distributed inductance and capacitance as a sensor.

5. The diagnostic test device of claim 1, further including means for housing said means for coupling radio frequency energy signals and said detector log amplifier for detecting the response to said radio frequency energy signals, and wherein said means for indicating the presence of flaws in the surface of said structure comprises optical indicator means mounted on the housing means.

6. The diagnostic test device of claim 1, wherein said means for indicating the presence of flaws in the surface of said structure comprises one optical indicator means for indicating no surface flaws and a second optical indicator means for indicating surface flaws.

7. The diagnostic test device of claim 5, further including means for coupling said means for determining whether the response signals indicate flaws in the surface of said structure to said means for indicating the presence of flaws in the surface of said structure.

8. The diagnostic test device of claim 1, wherein means for generating radio frequency energy signals comprises a voltage controlled oscillator for providing stepped frequency radio frequency energy signals.

9. The diagnostic test device of claim 1, wherein the means for generating radio frequency energy signals comprises a voltage controlled oscillator, an attenuator and a second amplifier.

10. The diagnostic test device of claim 9, further comprising a filter and a second attenuator connected in series with the detector log amplifier.

11. The diagnostic test device of claim 9, wherein the second amplifier is operated slightly above a 1 dB compression region.

12. The diagnostic test device of claim 1, further comprising a transfer switch for alternatively connecting the means for generating radio frequency energy signals to either the means for coupling the radio frequency energy signals into a surface of said structure, or the detector log amplifier for detecting the response to the radio frequency energy signals.

13. The diagnostic test device of claim 1, wherein the means for generating radio frequency energy signals includes a microprocessor, the microprocessor further performing energy signal analysis, and transmission of a signal representing the results of said analysis to said means for indicating the presence of flaws in the surface of said structure.

14. The diagnostic test device of claim 1 wherein said device includes a bellows for positioning said means for coupling the radio frequency energy signals flush with said surface of said structure.

15. The diagnostic test device of claim 1 wherein said device may be utilized on an extension pole.

16. The diagnostic test device of claim 1 wherein said device utilizes multiple sensor assemblies.

17. The diagnostic test device of claim 1 wherein said device utilizes sensor assemblies with multiple plug in sensor elements.

18. The diagnostic test device of claim 1, wherein the means for generating radio frequency energy signals further comprises:
- a microprocessor to generating a digital control signal; and
- a digital to analog converter for converting the digital control signal to an analog control signal.

19. The diagnostic test device of claim 18, further comprising:
- a voltage controlled oscillator for producing stepped frequency signals in response to the analog control signal, an attenuator for attenuating the stepped frequency signals, and an amplifier for amplifying the stepped frequency signals.

20. The diagnostic test device of claim 1, wherein the radio frequency energy signals comprise stepped frequency signals.

* * * * *